United States Patent [19]

Dahiya

[11] Patent Number: 5,362,638
[45] Date of Patent: Nov. 8, 1994

[54] FUNGAL STRAINS AND USE THEREOF IN ANTIBIOTIC PRODUCTION

[76] Inventor: Jagroop S. Dahiya, 33-2088 Pembina Highway, Winnipeg, Manitoba, Canada, R3T 2G8

[21] Appl. No.: 985,498

[22] Filed: Nov. 30, 1992

Related U.S. Application Data

[63] Continuation of Ser. No. 833,496, Feb. 10, 1992, abandoned.

[51] Int. Cl.$^5$ .................. C12P 17/06; C12N 15/10; C12N 15/80; C12N 1/15
[52] U.S. Cl. .................. 435/125; 435/172.2; 435/172.3; 435/254.3; 435/256.1; 435/913; 435/918; 935/52; 935/56; 935/60; 935/68
[58] Field of Search .......... 435/125, 172.2, 172.3, 435/254, 913, 918, 254.3, 256.1; 935/52, 60, 68, 89, 90, 92, 93, 97, 109; 536/23.2, 23.74

[56] References Cited

U.S. PATENT DOCUMENTS 4,294,926  10/1981  Monaghan et al. .................. 435/125
4,399,216   8/1983  Axel et al. ........................ 435/172.3

FOREIGN PATENT DOCUMENTS 1129794  8/1982  Canada .
1161380  1/1984  Canada .

OTHER PUBLICATIONS

J. F. Martin et al. "Organization and Expression of Genes Involved in the Biosynthesis of Antibiotics and other Secondary Metabolits" Ann. Rev. Microbiol. 43:173-206 (1989).
Gullo, V. P. et al. "High-Performance Liquid Chromatographic Analysis . . . " J. Chromatography 212:234-238 (1981).
Y. T. Hahn et al. "Genetic Transformation of a Arg B Mutant . . . " Appl. Environ. Microbiol. 54:1610-1611 (Jun. 1988).

*Primary Examiner*—Robert A. Wax
*Assistant Examiner*—Rebecca Prouty

[57] ABSTRACT

Lovastatin is produced by a process of fermentation using a fungal transformant produced by introducing into a non-lovastatin expressing Aspergillus strain such as a strain of *Aspergillus oryzae* the DNA of a lovastatin-expressing strain of *Aspergillus terreus*

11 Claims, 4 Drawing Sheets

FUNGAL STRAINS AND USE THEREOF IN ANTIBIOTIC PRODUCTION.

This application is a continuation of application Ser. No. 07/833,496, filed Feb. 10, 1992, now abandoned.

FIELD OF THE INVENTION

This invention relates to novel, genetically engineered fungal strains, and use thereof in preparation of antibiotics. More specifically, it relates to novel, genetically engineered strains of Aspergillus and their use in preparation of the drug lovastatin and analogs thereof.

BACKGROUND OF THE INVENTION

Lovastatin is, chemically [1S-[1α(R*),3α, 7β, 8β(2*, 4S*), 8aβ]]-2-methylbutanoic acid 1,2,3,7,8,8α-hexahydro-3,7-dimethyl-8-[2-(tetrahydro-4-hydroxy-6-oxo-2H-pyran-2-yl)-ethyl]-1-naphthalenyl ester, and has the chemical formula:

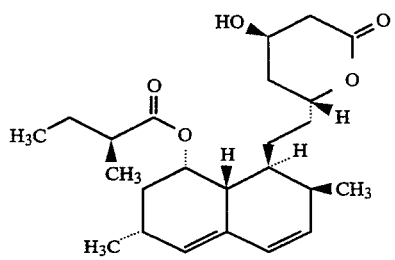

It is useful as an antihypercholesterolemic, being a potent inhibitor of HMG-CoA reductase, the rate controlling enzyme in cholesterol biosynthesis. It is a fungal metabolite produced by fermentation processes using selected fungal strains.

Antibiotics such as lovastatin are metabolites which require sets of several enzymes for their synthesis. To permit their production by molecular cloning of antibiotic-producing microorganisms requires the isolation, analysis and, perhaps modification of the corresponding genes for the several enzymes. Attempts to isolate such genes from such fungal species have so far yielded clones carrying either individual genes of the set, or only incomplete gene sets - see Malpartida and Hopwood, "Molecular Cloning of the Whole Biosynthetic Pathway of a Streptomyces Antibiotic and its Expression in a Heterologous Host", Nature (1984), 309 pp 462-464.

BRIEF REFERENCE TO THE PRIOR ART

Canadian Patent 1,129,794 Endo, describes the preparation of lovastatin by fermentation using a strain of the fungal species *Monascus ruber*.

Canadian Patent 1,161,380 Monaghan et al., describes the preparation of lovastatin by fermentation using strains of the fungal species *Aspergillus terreus*.

In both of these prior art processes, lovastatin is produced along with other, very similar chemical compounds, in substantial quantities, from which it must be separated. In its production using *Monascus ruber*, lovastatin co-occurs with monacolin J. In its production using *Aspergillus terreus*, it co-occurs with dihydrolovastatin and with the hydroxy acid. Whilst the hydroxy acid can be readily lactonized to lovastatin, the dihydrolovastatin must be separated from it.

SUMMARY OF THE INVENTION

It is an object of the present invention to provide novel, genetically engineered mutant fungal strains capable of use in fermentation processes to make lovastatin.

It is a further object of the invention to provide novel processes for making lovastatin by fermentation using such strains.

According to one aspect of the present invention, novel mutant fungal strains of the genus Aspergillus are provided, which are capable of expressing and secreting lovastatin. These strains contain the genes of the lovastatin-producing enzyme set, in functioning relationship, derived from the DNA of lovastatin-producing *Aspergillus terreus* strains. They are produced by a process of transformation of the DNA from the lovastatin-producing *Aspergillus terreus* strain, also containing an appropriate selectable marker, with another, non-lovastatin producing Aspergillus species, selection of the transformants so formed on the basis of the selectable marker, identification and isolation of the lovastatin-producing transformants and sub-cloning thereof.

According to another aspect of the invention, there is provided a process of preparing lovastatin which comprises fermenting a nutrient medium with a transformant Aspergillus microorganism containing genes derived from *Aspergillus terreus* and coding for the set of lovastatin-producing enzymes, and recovering the lovastatin so formed.

BRIEF REFERENCE TO THE DRAWINGS

DESCRIPTION OF THE PREFERRED EMBODIMENTS

Figure 1A:
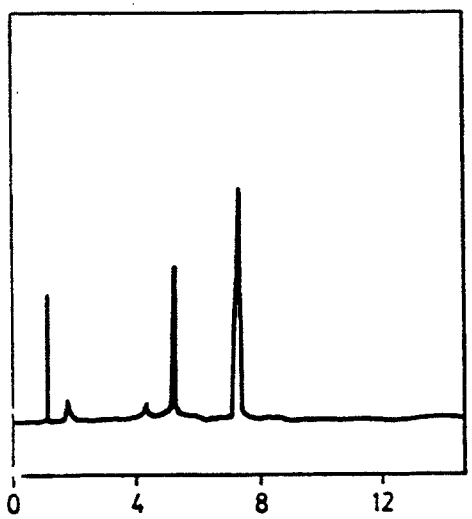
FIGS. 1A–1D are a graphical presentation of the HPLC analysis of the crude fungal extracts produced according to the Example 1 experiments described below.
Figure 1C:
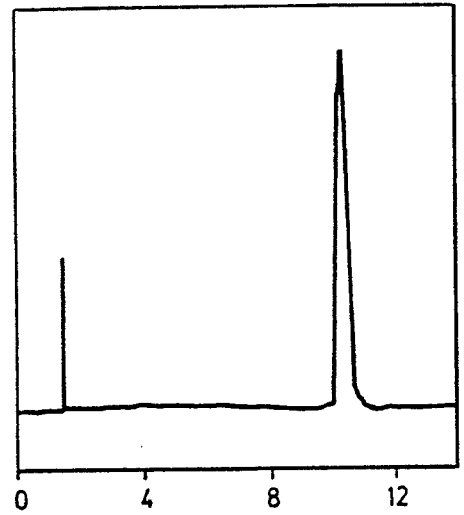
Figure 1B:
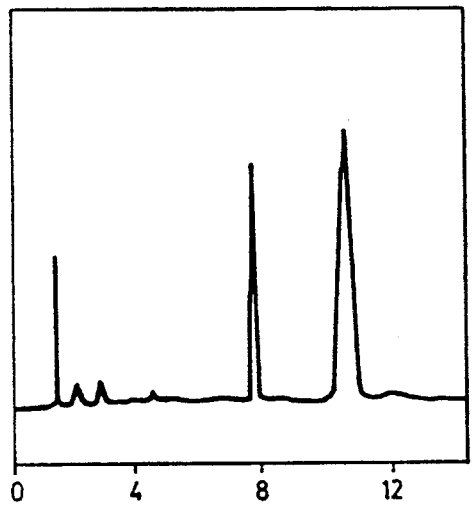
Figure 1D:
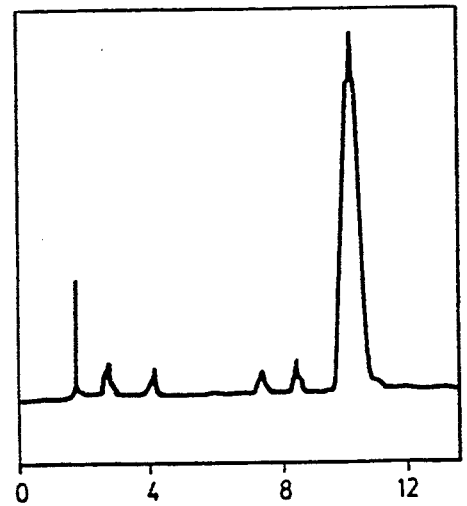

In the process of making the transformants of the present invention, standard techniques of preparing protoplasts from the selected, non-lovastatin producing Aspergillus strain, and standard techniques of extracting the DNA from the lovastatin-producing *Aspergillus terreus* strain can be employed. These techniques are well known to those of skill in the art and do not need detailed discussion herein. Similarly, the techniques and procedures of transformation useful herein are known and standard.

The preferred choice of non-lovastatin producing Aspergillus strain is a strain of *Aspergillus oryzae*, but this is not critical to success in practising the invention. Other species of Aspergillus such as *A. niger, A. nidulans, A. fumigalis* etc., can be used, since they are all sufficiently compatible with the DNA from *A. terreus* that transformation therewith can be accomplished successfully. *A. oryzae* is chosen as the preferred species on account of its inertness, which renders it easy and safe to handle in the laboratory and in commercial scale fermentations.

In order to select transformant microorganisms from non-transformants after the transformation process, the DNA from the *A. terreus* should contain a selectable marker. There is a wide choice of selectable markers available to and selectable by the skilled worker, and the precise choice is not critical to success in working the invention. Markers of antibiotic resistance such as ampicillin resistance, rifampicin resistance, streptomycin resistance etc. can be used, and the resulting mixture of transformants and non-transformants can be cultured in a medium containing the appropriate antibiotic, so that only the transformants, which contain the selectable marker, will survive for isolation.

Particularly preferred as a selectable marker, on the basis of convenience, is cycloheximide resistance. Cycloheximide is an inhibitor of protein synthesis, so that the presence of a cycloheximide-resistant strain or transformant in a culture broth is readily detected.

After selection of the transformants on the basis of the selectable marker, they are screened for those which will express and secrete lovastatin. Only a relatively small number of the total transformants produced in the transformation process have this capability. They are recognized by separate culturing in standard culture broth, and analysis of the resulting medium, e.g. by HPLC, for the presence of lovastatin. Those testing positive for the presence of lovastatin are sub-cultured and grown, to yield colonies of novel, lovastatin-producing transformant fungal microorganisms of the Aspergillus genus and preferably of the Aspergillus oryzae species.

The invention is further described for illustrative purposes in the following experimental accounts.

DESCRIPTION OF THE MOST PREFERRED EMBODIMENTS

Example 1

MATERIALS AND METHODS

FUNGAL CULTURE - fungal isolates Aspergillus terreus and A. oryzae used in the present study were isolated from orchard soil samples collected from Agriculture Canada, Research Station, Beaverlodge, Alberta, Canada.

SELECTION OF CYCLOHEXIMIDE RESISTANT MUTANTS

Having grown both Aspergilli isolates on Czapek's dox media containing cycloheximide (conc. 0.1–5 mM) for 6 days at 28°±2° C., Spores ($10^8$) of each isolate A. terreus and A. oryzae were dispensed on 10 mM cycloheximide Czapek's dox broth (50 ml) and incubated for 30 min., centrifuged at 10,000 g for 10 min., and then re-suspended in sterile distilled water. They were washed three times by agitation and resedimented by centrifugation. The spores were then suspended in sterile 1%(v/V) Triton X-100 solution and their numbers determined in an aliquot on a haemocytometer. An appropriate dilution was dispensed on the 10 mM cycloheximide selection medium and resistant mutants were isolated after 10 days of incubation at 28°±2° C. Isolates were examined for lovastatin production. A. cycloheximide resistant lovastatin producing isolate of A. terreus was selected for further transformation study.

PROTOPLAST AND DNA PREPARATION

Aspergillus oryzae and the cycloheximide-resistant lovastatin-producing A. terreus (herein designated JAG-4703) isolate were cultured separately in 50 ml of Czapek's dox broth. The cultures were incubated for 58 hours at 28°±2° C. on a rotary shaker (New Brunswick Scientific Inc.) at 200 rpm, then harvested and washed with sterile distilled water by repeated centrifugation.

Protoplasts from cultures of both species were obtained by using Novozym 234 (Novo-Nordisk, Novo Alle, DK 2880, Bagsvaerd, Denmark) to remove the cell walls during 10–12 hour digestion, generally following the method described by Dickinson & Isenberg, J. Gen. Microbiol. 128, p. 651–654 (1982). Aliquots of protoplasts from each species regenerated viable, single cell walled spores at 28° C. after 24 hours in regenerating medium(R) containing 0.1 g agar (Difco) 5g sorbose and 0.35 g EDTA in 50 ml distilled water. On germination these spores developed all the cultural characteristics of their parents.

The total DNA was isolated from Aspergillus terreus protoplasts according to the procedure described by Schlief & Wensink, "Practical Methods in Molecular Biology" 33, 21–29 (1981) The protoplasts were suspended in a solution consisting of 10 mg/ml SDS, 0.1 M NaCL and 0.1 M tris-HCL, pH 9.0. An equal volume of phenol saturated with the tris-HCL buffer was added. The mixture was centrifuged at 12,000 g for 10 min. in an Eppendorf Centrifuge tube (Brinkmann Instruments, Canada Ltd., Rexdale, Ontario). The upper phase, containing the DNA, was removed, mixed with 95% ethanol, stored at −20° C. for 60 min., then centrifuged as before for 10 min. The pellet was resuspended in buffer, pH 7.0, and incubated with. RNase (Sigma, St. Louis, MO, U.S.A.) treated with phenol and the DNA precipitated from the aqueous layer. The isolated DNA was purified by adsorption and washing on DEAE-cellulose (DE-52, Whatman), presoaked in 10mMtris-HCL buffer, pH 7.5 and 0.3M NaCL and contained in a pasteur pipette. The DNA was eluted with 10 mM tris-HCL buffer, pH 7.5 containing 1.5 M NaCL. This solution was diluted to 0.2 M NaCL and the DNA was precipitated with two volumes of ethanol. The purity of the DNA was estimated from the 200–320 nm spectra by determining the $A_{260}/A_{280}$ absorbance ratio. Only DNAs with ratios between 1.50 and 2.00 were used in the transformations. Six samples, each 0.1 mg of the isolated DNA were incubated in the regenerating medium to ensure the absence of viable protoplasts and none of them developed any colony.

PROTOPLAST-DNA INCUBATION

Approximately $5.2 \times 10^4$ A. oryzae protoplasts, estimated by haemocytometer counts, were incubated with 10–100 ng of A. terreus DNA in 5 ml regenerating medium, the composition of which was as described above, and regenerated as described above. In order to study the possible chemical effects of DNA on lovastatin expression, 10–100 ug calf-thymus DNA (Sigma Chemical Co., St. Louis, MO., U.S.A.), DNA (Bethesda Research Laboratories, Gaitherberg, MD, U.S.A.) and homologous A. orzyae DNA were incubated with similar lots of A. oryzae protoplasts. When DNA was included in the incubations, protoplast regeneration was reduced to less than 10% and comparable numbers of such treated protoplasts ($10^5$) failed to yield any cycloheximide resistance.

LOVASTATIN PRODUCTION AND ASSAY

The suspension of spores developed from A. oryzae protoplasts incubated with A. terreus DNA was inoculated, 1 ml per petriplate, onto Czapek'dox agar medium containing 10 mM cycloheximide. After incubation for 48 hours at 28°±2° C., cultures attained a diameter of 6–8 mm. Each developed separately from a single spore under these conditions. Those which grew on the cycloheximide medium were each inoculated separately onto Czapek'dox media broth (50 ml in 500 ml Erlenmeyer flask), incubated on rotary shaker (200 rpm) at 28°±2° C. for 12 days. Each growth media were examined for lovastatin production by the procedure described below and HPLC analysis.

EXTRACTION

Fermented broth (50 ml) was acidified to pH 4.0 with 17N HCL and then fractionated against ethylacetate (100ml, 3×). Pooled ethylacetate fractions were dried in vacuo at 30° C., the residue was collected in acetonitrile (5 ml) and then subjected to HPLC analysis.

HPLC ANALYSIS

The HPLC equipment (Beckman Model 420) was supplied by Beckman Instruments, Toronto, Canada and consisted of an Altex pump (Model 110 A) and injection valve. The LC-UV detector was set at 237 nm. A hypersil C-18 ODS silica column (25×0.46cm, i.d.) and a solvent system of acetonitrile and water (55:45,v/v) at flow rate of 1.0 ml/min. were used. Lovastatin produced was compared and quantitated from a standard lovastatin curve constructed.

Example 1 — Results

Seventy-nine cycloheximide-resistant isolates, including four lovastatin-producing isolates, were obtained from $5.2 \times 10^5$ A. oryzae protoplasts incubated with the DNA from the cycloheximide-resistant lovastatin-producing mutant of A. terreus. The transformation experiments were performed six times.

The results are given in the following Table 1.

TABLE 1

Cycloheximide-resistant and lovastatin-expressing Aspergillus oryzae protoplasts incubated with DNA from the cycloheximide-resistant lovastatin-producing mutant of Aspergillus terreus.

| Expt. # | Protoplasts · ml | Number of protoplasts Regenerated, After Protoplast Fusion, #/ml | % Regeneration | DNA (ng) | Number of Lovastatin-Producing Isolates |
|---|---|---|---|---|---|
| i) | $7.4 \times 10^5$ | $4.1 \times 10^5$ | 56 | 100 | 0 |
| ii) | $5.2 \times 10^5$ | $3.1 \times 10^5$ | 60 | 75 | 2 |
| iii) | $5.2 \times 10^5$ | $3.7 \times 10^5$ | 72 | 50 | 2 |
| iv) | $4.0 \times 10^5$ | $2.7 \times 10^5$ | 70 | 25 | 0 |
| v) | $2.6 \times 10^5$ | $1.5 \times 10^5$ | 65 | 10 | 0 |
| vi) | $1.6 \times 10^5$ | $1.1 \times 10^5$ | 70 | 0 | 0 |

One of the transformed culture AO-II, retained its original transformed characteristics for six months. FIG. 1 illustrates the HPLC analysis of the extracts obtained from the recipient and donor cultures of A. oryzae, and those treated with A. terreus DNA. The production of lovastatin by transformed isolates is shown below in Table 2.

TABLE 2

Lovastatin production by transformed isolates of Aspergillus oryzae in Czapek'dox broth (pH 6.8)

| Isolate # | Lovastatin Yield (mg/l) |
|---|---|
| AO-I | 15.36 ± 1.78 |
| AO-II | 26.89 ± 3.76 |
| AO-III | 13.46 ± 4.56 |
| AO-IV | 9.67 ± 0.75 |

Isolate no. AO-I was sub-cultured five times, to yield a transformant AoAt - NBJ/5 which has been deposited as a viable, permanent culture thereof with American Type Culture Collection under reference no. 74135.

The lovastatin is produced in association with the hydroxy acid analog thereof, which is readily convertible to lovastatin e.g. by refluxing in toluene, to accomplish lactonization and thereby to increase the lovastatin yield. The lactonization was not undertaken in these experiments.

Lovastatin produced by A. terreus parent culture in Czapek'dox broth was 166.72±5.92 mg/l, and parent A. oryzae did not produce any lovastatin.

Figure 2:
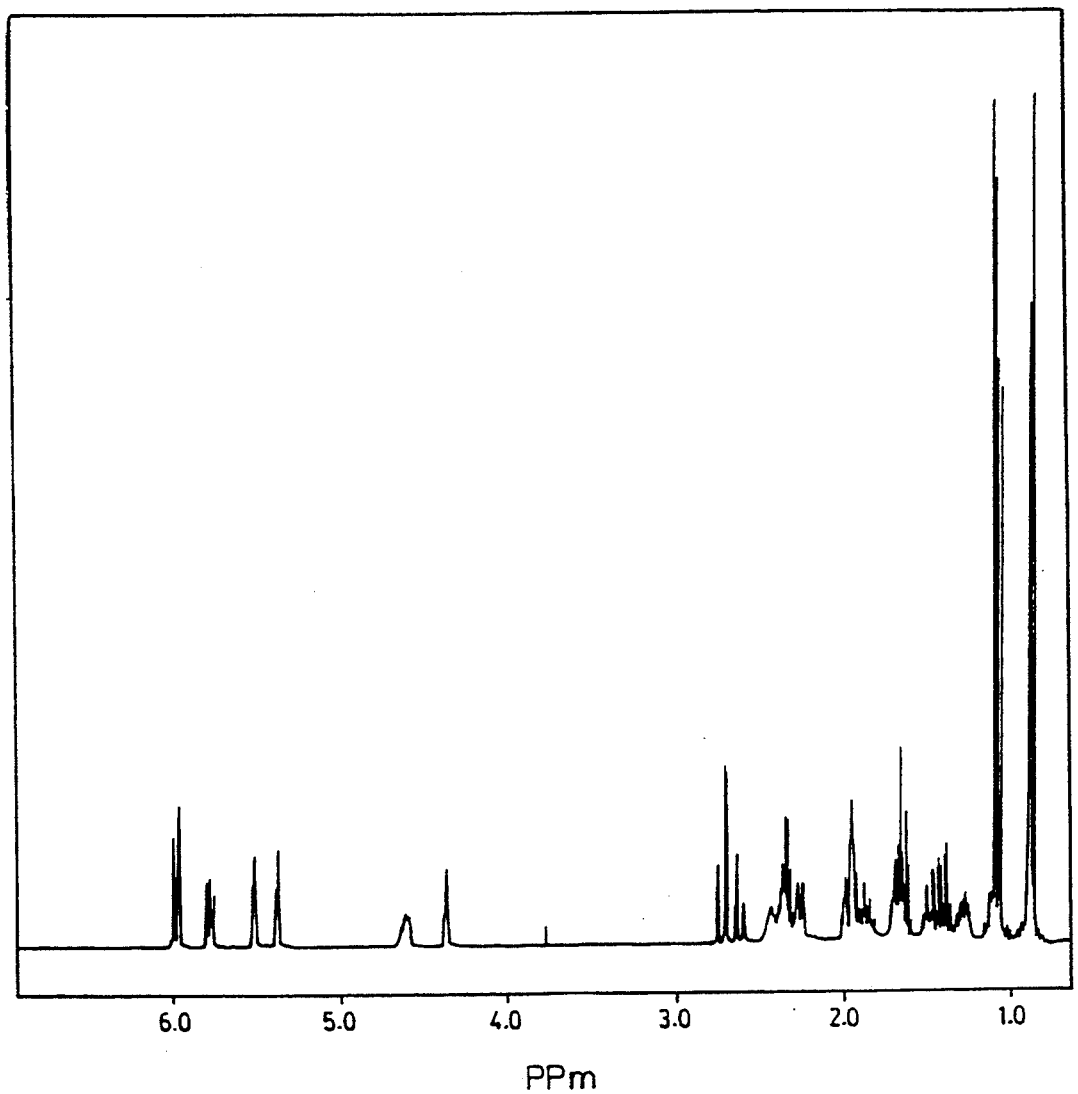
FIG. 2 is the $^1$H-NMR spectrum of the lovastatin compound obtained and purified from the hybrid strain.

FIG. 2 of the accompanying drawings is the $^1$H-NMR spectrum of the lovastatin compound purified by HPLC from the hybrid strain. By comparison with the known, standard spectrum of lovastatin, this spectrum confirms the identity of the product.

Figure 3:
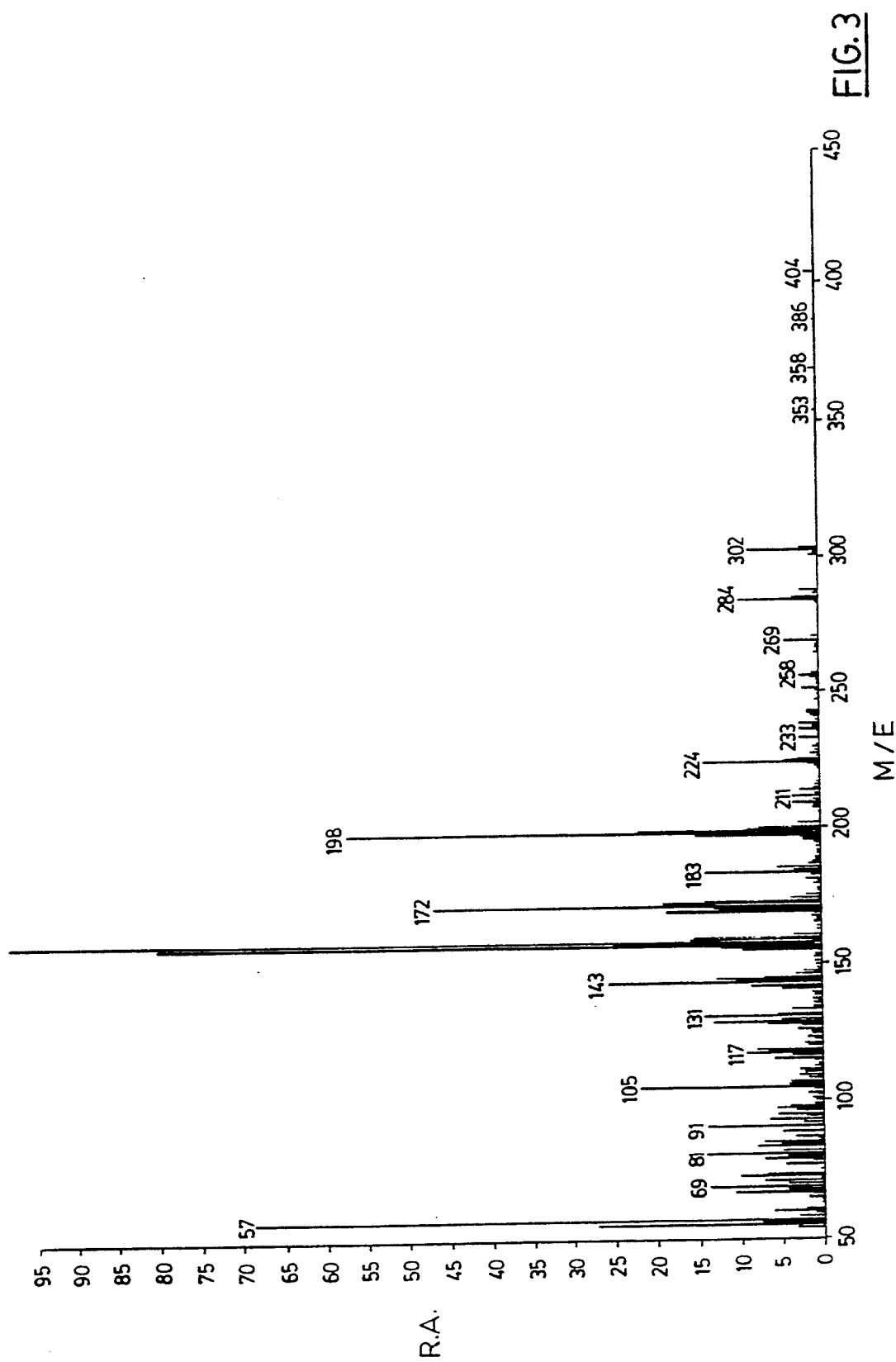
FIG. 3 is the mass spectrum of the same compound.

FIG. 3 of the accompanying drawings is the mass spectrum of the same product, and shows that lovastatin was obtained at a purity of 99%.

Concentrations of DNA ranging from 5–20 ng per ml of medium affected neither the regeneration capacity of the A. oryzae protoplasts nor the recovery of cycloheximide resistant and lovastatin-producing isolates from incubations with A. terreus DNA. The data indicate that these concentrations were not a limiting factor in the production of lovastatin. Similarly, DNA from calf-thymus, DNA and homologous A. oryzae DNA at concentrations from 5 ng to 5 ug per ml of medium did not affect the regeneration of A. oryzae protoplasts when compared with untreated controls. However, DNA at 10 and 100 ug per ml of medium reduced regeneration to maximum of 26% and 1% respectively. These DNA treatments did not elicit lovastatin expression.

The regenerating medium yielded numbers of protoplasts comparable to those obtained by Acha et al. J. Gen. Microbiol., 45, 515–523 (1966), using a more complex mineral medium. Conidia and freshly germinated conidia produced better yields of viable protoplasts and of DNA than the mycelia. The formation of cellular aggregates during protoplast regeneration described by Acha et al. (1966) was not observed in this system. The apparent transfer of factors responsible for the expression of cycloheximide resistance and lovastatin expression from A. terreus to A. oryzae indicates interspecies DNA transformation. The co-transformation of cycloheximide resistance and lovastatin production was unexpectedly satisfactory and suggests a physical proximity and possible clustering of the genes involved in the expression of these characteristics.

Figure 4:
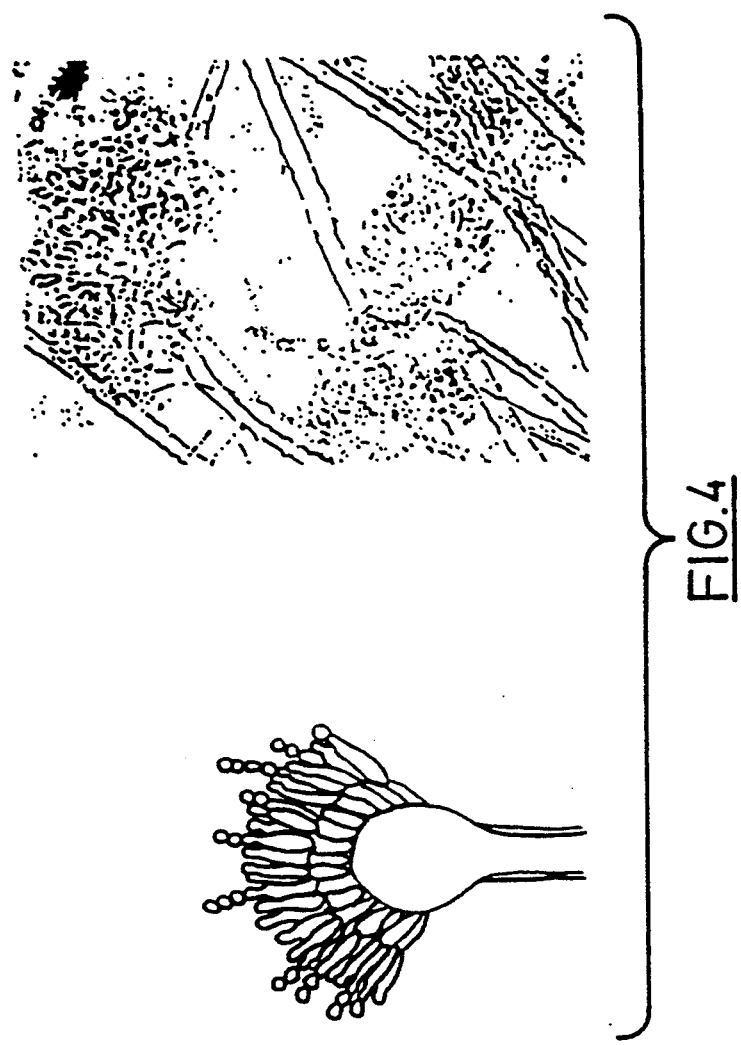
FIG. 4 is a depiction of the morphological characteristics of novel transformant AoAt/NBJ-V.

The morphology of the novel transformant AoAt-NBJ/5 is depicted in FIG. 4 and may be characterized as follows:

MORPHOLOGY OF AoAt-NBJ/5

Conidial heads columnar, light brown. Conidiophores smooth, colourless. Vesicles hemispherical, covered up to one-half or two-thirds by phialides arranged in two layers. Conidia globose or ellipsoidal, smooth colonies on Czapek agar growing very rapidly, either floccose or velvety cinnamon brown due to production of conidia. Orange exudate, reverse yellow to brown.

These experiments demonstrate that, in principle, genetically determined antibiotic producing characteristics of one fungal species can be expressed in another.

Example 2

FERMENTATION PROCESS FOR LOVASTATIN PRODUCTION

Grow the variant AoAt-NBJ/V fungal isolate onto PDA (potato-dextrose agar) slant for 6 days at 25° C. Prepare conidial suspension (conidial count $10^8$–$10^9$/mL) and transfer 10 mL of the suspension into Erlenmeyer flask containing 50–60g of autoclaved rice seed. Shake it vigorously for 2–3 minutes and incubate at 25° C. for 5–6 days. Examine microscopically the conidial morphology. Prepare conidial suspension (c.fou. count $1 \times 10^6$ conidial/mL) by suspending in Triton X-100 (0.001%, w/v) and inoculate (2–3%) into malt extract peptone (MEP) broth (pH 6.8) (10L). Allow the spores to germinate for 15–20 hours (rpm 200) at 28° C. (% D.O. 40–60%). Transfer the germinated spore (10L) to 100L of fresh MEP broth (pH 6.8) and allow to grow for a further 24–48 hours at 28° C. (rpm 100). After incubation for 24–48 hours, transfer this fungal broth (100L) into a 1000L (working volume) capacity fermenter containing production media (pH 6.8) and allow it to ferment for further 5–7 days at 28° C. (% D.O. 40–60%) and agitation rate (40–50 rpm). The pH of the fermenting broth should be adjusted (between pH 6–6.8) with IN NaOH solution.

DOWNSTREAM PROCESS

A. ISOLATION OF THE PRODUCT

Fermented broth is acidified with HCl (conc.) (or with sulphuric acid) to pH 3.0. The acidified broth is filtered or centrifuged to remove most of the aqueous phase.

B. LACTONIZATION OF THE ACIDIC FORM OF LOVASTATIN INTO LACTONE FORM

The solid residues are suspended in toluene and the suspension is warmed to the temperature of reflux with simultaneous elimination of water by azeotropic toluenewater distillation. During this phase, the acidic form of the product is dissolved in toluene and simultaneously transformed into lovastatin by lactonization and concomitant loss of water.

C. PURIFICATION

The crude lactonized product is recrystallized two to three times to obtain 98–99% pure lovastatin.

(i) The lovastatin (crude) is dissolved at $\approx$ 55° C. in a solution of water-methanol/acetonitrile) and the mixture is filtered, while hot, through a bed of absorbent solid activated carbon. The filtrate is cooled and water added to obtain recrystallization and the mixture is cooled to 15° C. to complete the process.

The lovastatin is then collected by filtration, washed in a solution of cold water-methanol/acetonitrile and dried in vacuo between 40° and 50° C.

(ii) The dried lovastatin is dissolved in ethylacetate at about 65° to 70° C. The solution is filtered and the filtrate is cooled to about −10° C. to crystallize the lovastatin, which is obtained by filtration, washed with cold ethylacetate, and dried in vacuo between 40°–50° C. The whole process is repeated and then water soluble impurities are removed by rinsing the crystals with deionized water.

Whilst the invention has been described in detail by references of specific experiments, it will be understood that it is not restricted thereto. Its scope is defined in the appended claims.

I claim:

1. A process of preparing lovastatin which comprises fermenting a nutrient medium with a transformed fungal microorganism of an Aspergillus strain naturally incapable of expressing lovastatin but which has been transformed to contain foreign DNA derived from a lovastatin-producing Aspergillus terreus species and coding for the enzymes capable of synthesizing lovastatin, and a selectable marker, and recovering the lovastatin from the nutrient medium.

2. The process of claim 1 wherein the Aspergillus strain naturally incapable of expressing lovastatin is a strain selected from the group of species consisting of *A. oryzae, A. niger, A. nidulans* and *A. fumigalis*.

3. The process of claim 2 wherein said Aspergillus strain is a strain of the species *A. oryzae*.

4. The process of claim 3 wherein the foreign DNA introduced into the transformant contains cycloheximide-resistance genes as selectable marker.

5. The process of claim 4 wherein the transformant is ATCC 741356.

6. The process of claim 5 including the additional step of lactonization of the hydroxyacid analog formed in the fermentation process to lovastatin.

7. Fungal transformants capable of expressing the enzymes for synthesizing lovastatin, said transformants being strains of an Aspergillus sp. naturally incapable of lovastatin expression but containing foreign DNA derived from a lovastatin producing *Aspergillus terreus* strain and containing genes coding for the enzymes capable of synthesizing lovastatin.

8. Fungal transformants according to claim 7 wherein the Aspergillus sp. is selected from the group consisting of *A. oryzae, A. niger, A. nidulans* and *A. fumigalus*.

9. Fungal transformants according to claim 8 wherein the Aspergillus sp. is *A. oryzae*.

10. Fungal transformants according to claim 9, and comprising the product of transfection of total DNA from said *A. terreus* strain into said *A. oryzae* strain.

11. The fungal transformant ATCC 74135.

* * * * *